United States Patent [19]

Buckler et al.

[11] 4,273,715
[45] Jun. 16, 1981

[54] N-(HYDROXYALKYL)-7-HYDROXYCOUMARIN-3-CARBOXAMIDES

[75] Inventors: Robert T. Buckler, Edwardsburg, Mich.; John F. Burd, Elkhart, Ind.

[73] Assignee: Miles Laboratories, Inc., Elkhart, Ind.

[21] Appl. No.: 140,019

[22] Filed: Apr. 14, 1980

[51] Int. Cl.$^3$ .............................................. C07D 311.16
[52] U.S. Cl. ........................ 260/343.45; 252/301.17; 435/7
[58] Field of Search .................................... 260/343.45

[56] References Cited

U.S. PATENT DOCUMENTS

| 3,293,255 | 12/1966 | Molho et al. | 260/343.45 |
| 3,511,856 | 5/1970 | McIntyre et al. | 260/343.45 |
| 4,078,075 | 3/1978 | Beriger | 260/343.45 |

OTHER PUBLICATIONS

Katsumi et al., Chem Abst. vol. 81 1974 86751c.

*Primary Examiner*—Henry R. Jiles
*Assistant Examiner*—Jane T. Fan
*Attorney, Agent, or Firm*—Andrew L. Klawitter

[57] ABSTRACT

Title compounds of the formula:

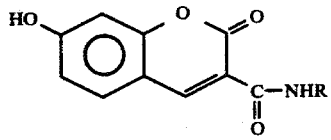

wherein R is hydroxy substituted lower alkyl. The compounds have advantageous water solubility and spectral characteristics for use as instrument calibrators for certain homogeneous fluorescent immunoassays.

3 Claims, No Drawings

N-(HYDROXYALKYL)-7-HYDROXYCOUMARIN-3-CARBOXAMIDES

BACKGROUND OF THE INVENTION

The present invention relates to fluorescent coumarin derivatives useful as instrument calibrators for certain homogeneous fluorescent immunoassay test procedures. In particular, the present compounds have advantageous water solubility and spectral characteristics as instrument calibrators for use in conjunction with certain homogeneous enzyme substrate-labeled fluorescent immunoassay methods.

In September 1979, the first product in the series of AMES TDA TM therapeutic drug assay test kits (Miles Laboratories, Inc., Elkhart, IN) was introduced, the AMES TDA Gentamicin test kit. The assay method used with the test kit is a homogeneous enzyme-substrate-labeled fluorescent immunoassay (SLFIA) technique; "homogeneous" because there is no separation step required in performing the assay, in contrast with "heterogeneous" techniques such as the radioimmunoassay (RIA). A key reagent in the test kit is a labeled conjugate comprising sisomicin (an aminoglycoside antibiotic which behaves immunochemically like gentamicin) covalently bound to a derivative of the fluorogenic enzyme substrate umbelliferyl-β-D-galactoside. This Fluorogenic Gentamicin Reagent (FGR) is non-fluorescent under the conditions of the assay, however, hydrolysis catalyzed by β-galactosidase yields a fluorescent product. When antibody to gentamicin binds FGR, it becomes virtually inactive as a substrate for β-galactosidase.

Competitive binding reactions are established with a constant amount of FGR, a limiting amount of the antibody, and the test sample containing gentamicin:

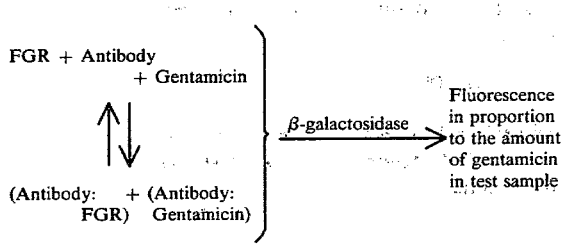

The gentamicin in the test sample competes with FGR for binding to antibody. FGR not bound by antibody is hydrolyzed by β-galactosidase to produce the fluorescent product. Hence the fluorescence produced is dependent on the gentamicin level in the sample. The fluorescence intensity is related to gentamicin level by means of a standard curve.

Fluorescence is measured on a fluorometer and recorded in arbitrary fluorescence units. In order that the instrument operator can properly set the instrument to the appropriate scale multiplier prior to reading the first actual assay result, the AMES TDA Gentamicin product includes a Range Adjustment Solution (RAS) comprising the fluorescent compound N-(phenyl)-7-hydroxycoumarin-3-carboxamide. The concentration of this fluorescent compound in the RAS is set such that the resulting fluorescence intensity of a prescribed diluted volume of the RAS under the conditions of the assay, i.e., room temperature, excitation wavelength of 400 nm and emission wavelength of 450 nm, approximates the fluorescence of the highest gentamicin level on the standard curve. Thus, the operator can preset the instrument to the maximum useable scale for actual assay runs. In addition, instrument function can be tested by assaying a series of dilutions of the RAS and checking the expected linearity of the relationship between observed fluorescence and RAS level.

Although the RAS compound, N-(phenyl)-7-hydroxycoumarin-3-carboxamide, is commercially available and has the desired spectral characteristics, its water solubility is quite poor for manufacturing purposes. Accordingly, it is the object of the present invention to provide compounds having the desired spectral characteristics for use in the Range Adjustment Solution together with increased water solubility, yet not involving a delicate or intricate synthesis.

SUMMARY OF THE INVENTION

The present invention provides compounds of the formula:

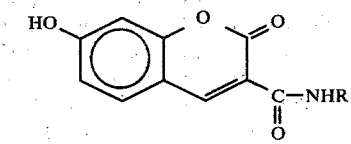

wherein R is hydroxy substituted lower alkyl, i.e., a mono- or poly-hydroxy substituted radical, with lower alkyl referring to alkyl of 1 to 6 carbon atoms, including linear and branched types. In the preferred N-(hydroxyalkyl)-7-hydroxycoumarin-3-carboxamides, R is of the formula

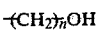

wherein n is an integer from 2 through 6 inclusive, more usually 2 through 4, and most preferably 2. The present compounds have been found to be about twice as fluorescent on a molar basis compared to N-(phenyl)-7-hydroxycoumarin-3-carboxamide and about 200 times more water soluble.

The present compounds are conveniently prepared by reacting 7-hydroxycoumarin-3-carbonyl chloride [Sherman et al, Anal. Chem. 40:803(1968)] with an appropriate aminoalkanol in a nonaqueous solvent, usually dioxane, at lowered temperatures, usually around 0° C. The aminoalkanol will be a mono- or poly-hydroxy substituted, linear or branched, lower alkane (consisting of 1–6 carbon atoms). Representative of such aminoalkanols are 2-aminopropanol, 3-aminopropanol, 2-amino-1-butanol, 3-amino-1-butanol, 4-amino-1-butanol, 2-amino-2-methyl-1-propanol, 2-(aminomethyl)-2-propanol, 2-amino-4-methyl-1-pentanol, 5-amino-1-pentanol, 6-amino-1-hexanol, and tris-(hydroxymethyl)-aminomethane. The preferred aminoalkanols are the mono-substituted linear alkanols, with 2-aminoethanol being most preferred.

The present invention will now be illustrated, but is not intended to be limited, by the following example.

Preparation of
N-(2-hydroxyethyl)-7-hydroxycoumarin-3-carboxamide

To a cold, stirred solution of 3.05 grams (g) [0.05 mole (mol)] of 2-aminoethanol in 30 milliliters (ml) of dioxane was added a suspension of 2.2 g (0.01 mol) of 7-hydroxycoumarin-3-carbonyl chloride [Sherman et al, Anal. Chem. 40:803(1968)] in 75 ml of dioxane. The mixture was stirred at 0° C. for 30 minutes, during which time a thick oil precipitated that solidified upon scratching with a spatula. The dioxane was decanted and the precipitate dissolved in water. Adjustment of the pH of the aqueous solution to 7.0 with glacial acetic acid resulted in precipitation of a tan solid. The solid precipitate was recrystallized from water to give 1.3 g (52% yield) of N-(2-hydroxyethyl)-7-hydroxycoumarin-3-carboxamide as a white solid with a melting point of 244°-245° C. Elemental analysis and infrared spectral data for the product are given below:

Calculated for $C_{12}H_{11}NO_5$: C, 57.83; H, 4.45; N, 5.62. Found: C, 57.83; H, 4.47; N, 5.57.

Infrared Spectrum (KCl): 1700 cm$^{-1}$ (lactone CO); 1620 and 1545 cm$^{-1}$ (amide CO).

Use in Range Adjustment Solution

N-(2-Hydroxyethyl)-7-hydroxycoumarin-3-carboxamide is dissolved in formate buffer to form a Range Adjustment Solution (RAS). The concentration of the carboxamide derivative is adjusted so that the fluorescence of a solution formed by mixing 3 ml of buffer with 100 μl of the RAS is approximately equal to the fluorescence produced in running an assay with the highest standard in an AMES TDA test kit (Miles Laboratories, Inc., Elkhart, IN). The RAS is used in the set-up and fluorescence check procedure for the Aminco-Bowman Spectrophotofluorometer (American Instrument Co., Silver Springs, MD) which is performed prior to the running of AMES TDA assays. The procedure is as follows:

1. Warm-up and operate the spectrophotofluorometer according to the manufacturer's intructions.
2. Set the excitation monochromator at 400 nm and the emission monochromator at 450 nm.
3. Exclude light from the photodetector and set the "Meter Multiplier" to the "Zero Adjust" position. Zero the meter with the "Zero Adjust" knob.
4. Turn the "Meter Multiplier" to the highest amplification setting and adjust the meter to zero percent transmittance with the "Dark Current" knob.
5. Pipette 3.0 ml of Diluted Buffer (0.05 M Bicine buffer, pH 8.5, containing 0.1% sodium azide) into each of five Spectrovette disposable plastic cuvettes (Evergreen Scientific, Los Angeles, Calif.) marked 0, 25, 50, 75 and 100 respectively.
6. Accurately add 25, 50, 75 and 100 μl of the RAS to the appropriately marked cuvettes. Gently mix the contents of each cuvette. After mixing, wait 5 minutes before taking fluorescence readings.
7. Place the "100" cuvette in the spectrophotofluorometer and select a "Meter Multiplier" setting which will give a reading of 100% when used in conjunction with the appropriate setting of the "sensitivity" adjust.
8. Measure the fluorescence of the remaining cuvettes and record the readings.
9. On linear graph paper, plot the fluorescence values on the y axis versus the amount of RAS in μl on the x axis. If proper technique was used and the instrument is operating properly, the above plot should yield a straight line.
10. If a linear response is obtained, performance of the assay with unknowns may proceed with the existing instrument settings.

Straight line plots of fluorescence versus μls of RAS were produced in using the RAS to set up the AMES TDA test kit assays.

What is claimed is:

1. A compound of the formula:

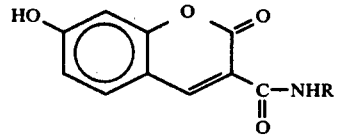

wherein R is hydroxy substituted lower alkyl.

2. The compound of claim 1 wherein R is of the formula:

wherein n is an integer from 2 through 6 inclusive.

3. N-(2-Hydroxyethyl)-7-hydroxycoumarin-3-carboxamide.